US006958422B2

(12) United States Patent
Noelke et al.

(10) Patent No.: US 6,958,422 B2
(45) Date of Patent: Oct. 25, 2005

(54) PYROLYSIS PROCESS

(75) Inventors: Charles Joseph Noelke, Wilmington, DE (US); Velliyur Nott Mallikarjuna Rao, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 10/738,491

(22) Filed: Dec. 17, 2003

(65) Prior Publication Data

US 2005/0137430 A1    Jun. 23, 2005

(51) Int. Cl.$^7$ ............... C07C 17/25; C07C 17/093; C07C 17/26; C07C 17/35; C07C 17/37

(52) U.S. Cl. ............ 570/172; 570/171; 570/175; 570/240

(58) Field of Search ............... 570/171, 172, 570/175, 240

(56) References Cited

FOREIGN PATENT DOCUMENTS

IN    158251    10/1986

*Primary Examiner*—Elvis O. Price

(57) ABSTRACT

The present invention relates to the pyrolysis of hydrochlorofluorocarbons to form fluoromonomers such as tetrafluoroethylene, the pyrolysis being carried out in a reaction zone lined with nickel and mechanically supported by a jacket of other corrosion resistant metal, the nickel lining providing an improved yield of valuable reaction products.

11 Claims, No Drawings

PYROLYSIS PROCESS

BACKGROUND OF THE INVENTION

1. Field of the Invention

This invention relates to the pyrolysis of hydrofluorocarbons or hydrochlorofluorocarbons.

2. Description of Related Art

Indian Patent Publication 158251 (1982) discloses the disadvantage of pyrolyzing chlorodifluoromethane (HCFC-22) to tetrafluoroethylene (TFE) in a platinum tube, namely of providing low conversion and the formation of corrosive products, such as HCl, and alleges to solve this problem by using a reactor tube consisting of nickel or a nickel alloy, after first preheating the HCFC-22 in the presence of copper to scavenge water vapor and form copper oxide. The Publication does not disclose any data to show the improvement over platinum. Moreover, the use of a nickel or nickel alloy tube cannot prevent the formation of HCl because the effect of pyrolyzing HCFC-22 ($CF_2HCl$) is to cause the HCl to split off from the HCFC-22, leaving the $:CF_2$ radical (carbene). The carbenes couple, forming TFE. It is apparent that the reference to a platinum reactor tube in the Publication is a reference to a small research pyrolysis tube, because the expense of platinum has lead the industry away from using this material in a commercial-size reactor. The same is true for nickel, not because of an expense issue, but because nickel lacks the strength and ductility for fabrication into a commercial-size reactor. Nickel alloy, notably Inconel® alloys containing 13–25 wt % Cr, with Mo and other metals, have been the industry standard material of construction for furnaces for the pyrolysis of hydrochlorofluorocarbons or hydrofluorocarbons to fluoromonomers such as TFE, such alloys having sufficient strength and ductility for fabrication and corrosion resistance under pyrolysis conditions to be useful in this application.

BRIEF SUMMARY OF THE INVENTION

The present invention arises from the discovery that a nickel lining instead of a nickel alloy lining provides improved selectivity to useful products from the pyrolysis of hydrochlorofluorocarbons and hydrofluorocarbons. It is not enough that conversion of the hydrochlorofluorocarbon or hydrofluorocarbon may improve in the pyrolysis process. It is most important that the reaction products produced are high value products, with undesirable by-products being minimized, that is, it is critical that conversion be selective, producing only desirable products to the greatest extent possible. Therefore good conversion as well as high selectivity are needed. Small percents of undesirable by-products present costly disposal problems, because the high production rates and long production runs result in the need to dispose of large amounts of undesirable by-products. Conversely, even a small improvement yield represents a high value improvement because of the accumulated large amount of high value product.

Thus, the present invention is the process comprising pyrolyzing hydrochlorofluorocarbon or hydrofluorocarbon to fluoromonomer, said pyrolyzing being carried out in a reaction zone lined with mechanically supported nickel. Nickel by itself as the material of construction of the reaction zone, e.g., the tubular reactor in which the pyrolysis is typically carried out, is unsuitable for commercial-size pyrolysis tubes. In accordance with the present invention, the nickel is present as a lining that is mechanically supported by a backing metal material of construction that provides the strength and ductility needed for fabrication of the reaction zone and its use. Thus, the process of the present invention, in terms of when the reaction zone is tubular in cross-section, includes a metal support for the nickel lining, the metal support supplying the necessary mechanical strength.

It is surprising that use of the mechanically supported nickel lining in the pyrolysis of hydrochlorofluorocarbons and hydrofluorocarbons gives greater yield of fluoromonomer and other high value reaction products than when nickel alloy is used as the surface of the reaction zone.

DETAILED DESCRIPTION OF THE INVENTION

With respect to the mechanically supported nickel-lining of the reaction zone, in a tubular reactor, i.e. when the reactor is a simple tube, the reaction zone will be tubular in shape. The cross-sectional shape of the tube will usually be round (circular), but may be in the form of other cross-sections such as elliptical. The reaction zone may also be annular in shape as is the case in reactors made up of concentric tubes (annular reactors), the inner tube having a heater at the center and the outer tube being heated on its outer surface. The reaction zone will generally be at least about 8 to 50 ft (2.4 to 15.24 m) long, preferably about 10 to 25 feet (3 to 8 m). In a reactor that is a simple tube, the width of the reaction zone is the inner diameter of the tube. In annular reactors, the width of the reaction zone is the thickness of the annular space, that is the distance between the outer surface of the inner tube, and the inner surface of the outer tube. The width of the reaction zone in a tubular reactor is at least about ¾ in (1.9 cm) and may be up to about 1 foot (30 cm). The width of the reaction zone in an annular reactor is from about 0.25 inch to 1 foot (60 mm to 30 cm). Many commercial-size pyrolysis tubes are longer and/or wider. Such tubular reactors have a surface (inner) to volume ratio of at least about 5 $in^{-1}$ (2 $cm^{-1}$). More particularly, the volume of the reaction zone, i.e. the volume of the tubular reactor, will generally be at least about 0.04 $m^3$ and more often at least about 0.2 $m^3$. The volume of annular reactors will be similar. The tubular reactor can be straight, or if of sufficient length, for space savings it can be in the form of a helical coil. Typically, such a coil is formed from straight lengths of tube by bending into the coil shape and welding the coiled shapes together end-to-end to form the helix, using Ni as the welding material. The helical tubular reactor of course forms a helical reaction zone (lined with Ni).

In a tubular reactor the inner surface is nickel and the outer surface is the supporting material. The mechanical support for the nickel lining can be a preformed outer tube, in which the lining is formed, an outer tube that is formed simultaneously with the lining, a preformed lining tube and outer support tube that are interfitted together and then adhered to one another, or a tube which is formed on the outer surface of the preformed tubular lining.

In an annular reactor, the outer tube is lined with nickel on its inner surface and the inner tube is lined with nickel on its outer surface, the result being that surfaces that define the annular space are nickel lined.

The thickness of the lining will depend on its method of formation. Intimate contact between the lining and the support tube is desired for the most efficient transfer of applied heat through the wall of the reactor. For example, the lining can be formed on the surface of the mechanical supporting tube, by plating by conventional means. Thicker Ni linings can be formed by coextrusion of the Ni lining and supporting tube. If the intimacy of contact between the lining and supporting tube is less than desired, i.e. the lining and support tube do not move together in the coiling operation, the lining can be welded to the support tube at its ends. Additional methods for achieving this intimate contact are explosive cladding and hydrodynamic expansion. The weld overlay method can also be used, wherein the supporting tube is formed over the outer surface of the pre-formed tube of lining material (Ni) by welding a continuous ribbon of the support metal to the outer surface of the lining tube as the metal ribbon is wound in abutting relationship around the outer surface of the lining tube, such as disclosed in U.S. Pat. No. 6,013,890. When used in making the inner tube of an annular reactor, the nickel lining is formed over the outer surface of the supporting tube. The weld overlay method is preferred. While the linings in abutting tube ends are welded together using Ni welds, the support tube is welded end-to-end using material similar to or the same as the material of construction of the support tube. The thickness of the lining is established based on estimates of the expected corrosion rate, and the thickness of the support material is established by the estimate of strength required to withstand the stresses expected to be experienced by the reactor in installation, operation and repair of the reactor. Generally, the thickness of the lining is at least about 0.001 in (0.0025 cm) thick and preferably at least about 0.030 in (0.076 cm) thick, and more preferably at least about 0.060 in (0.152 cm) thick, and may be as thick as about 1 in (2.54 cm) or thicker. The support tube will generally be at least about 1/16 in to 1 in (0.16–2.54 cm) in thickness. If the thermowells (housing for thermocouples communicating through the reactor wall thickness to the interior of the reactor) are not made of lining material because of their lack of strength, the material of construction of the thermowell can also be covered with nickel where exposed to the pyrolysis reaction.

The Ni lining will consist essentially of Ni, i.e. be free of impurities which have any appreciable adverse effect on the life of the lining under the conditions of the operation of the furnace. The Ni lining will not contain more than about 1 wt %, preferably no more than about 0.1 wt % of any other element, i.e. the Ni is not an alloy. If carbon is present in the Ni, the amount of carbon should be no greater than about 0.02 wt %, otherwise the carbon will render the Ni lining too brittle. Thus, the Ni used as the lining in accordance with the present invention, be at least about 99.8 wt % Ni. Ni is commonly available as Ni 200, Ni 201, and Ni 270, the last being the most pure. Ni 200 sometimes contains more than 0.02 wt % C and sometimes can be obtained containing no more than 0.02 wt % carbon content. Thus Ni 200 can be used when it contains no greater than about 0.02 wt % carbon. Ni 201 is preferred, however, based on economy and performance. Weight percents disclosed herein are based on the total weight of the Ni or total weight of the support metal (jacket), as the case may be.

A wide variety of support materials for the Ni lining can be used, such as stainless steel and Inconel® alloy, such as Inconel® 600, 601, and 617. The Inconel alloys typically contain 13 to 25 wt % Cr; alloys 600, 601, and 617 contain 16, 22, and 23 wt % Cr, respectively. The method of adhering the lining to the support material will depend on the particular support tube material of construction. If the reactor is to be a coil, coiling of the lined tube is done by conventional means. The support material should be oxidation resistant at the high temperatures applied to it in order to heat the reaction zone to the desired pyrolysis temperature. The support material also shields the surface of the lining facing the direction from which heat is applied from oxygen and thereby from oxidative degradation.

The tubular reactor forming the reaction zone used in the present invention is positioned within a housing that is equipped with means for heating the tubular reactor, such as hot gas passing between the outer surface of the coiled reactor and the inner surface of the housing or a radiant heat source positioned within the housing. The combination of the housing and tubular reactor contained within the housing can be considered the pyrolysis furnace. The annular reactor can be arranged similarly with the additional provision for heating the inside of the inner tube, such as with an electric heating element.

The Ni lining of the reactor, which defines the reaction zone, will usually be smooth to minimize the pressure drop of gases passing through the reaction zone.

A variety of hydrochlorofluorocarbons and hydrofluorocarbons can be pyrolyzed in the above-described reaction zone used in accordance with the present invention. The most common hydrochlorofluorocarbon that is pyrolyzed to fluoromonomer is chlorodifluoromethane (HCFC-22), yielding primarily TFE and a smaller amount of hexafluoropropylene, the amount depending on pyrolysis conditions adjusted to get the proportion of each fluoromonomer desired. Additional valuable pyrolysis reaction products that are formed are $CF_2ClCF_2H$ (HCFC 124a) and perfluorocyclobutane (c-318). The HCFC-124a and c-318 are themselves sources of fluoromonomer and can be recycled individually or collectively as a co-feed with the fed of principal hydrochlorofluorocarbon, such as HCFC-22 fed to the reaction zone. Other valuable pyrolysis reaction products that can be further reacted to make monomers include HFC-23, HCFC-124, HCFC-143a, and HCFC-226cb. The process of the present invention is conducted by continuously feeding hydrochlorofluorocarbon and/or hydrofluorocarbon into one end of the tubular reactor (reaction zone) and continuously withdrawing the unreacted hydrochlorofluorocarbon and/or hydrofluorocarbon and reaction products from the exit end of the reactor, whereby the reaction system within the reactor involves the continuous passage of these gases through the reaction zone. The separation and recovery of unreacted hydrochlorofluorocarbon and/or hydrofluorocarbon for recycle to the furnace, the fluoromonomers and other valuable reaction products, and disposal of undesirable by-products such as perfluoroisobutylene (PFIB), are done by conventional methods.

The process can be operated at a wide variety of temperature, pressure and contact time conditions, which are selected based on the volume of the furnace, to produce HFP most economically, including without producing an excessive amount of undesirable by-products. For hydrochlorofluorocarbons the temperature of the pyrolysis reaction will generally be at least about 600° C., and preferably no more than about 750° C. to minimize the formation of undesirable by-products.

Preferably, however, the pyrolysis reaction is conducted within the range of about 625° C. to 725° C. For hydrofluorocarbons the temperature of the pyrolysis reaction will generally be higher, at least about 750° C., and preferably at least about 800° C. to 900° C. For cofeeds of hydrochlorofluorocarbon or hydrofluorocarbon to the reactor, the preferred temperature is the temperature range used for hydrochlorofluorocarbons.

Typically, contact times (residence time within the reaction zone) will be less than about 0.1 second and preferably from about 60 to 100 milliseconds when the reactant is hydrochlorofluorocarbon. Hydrofluorocarbons may require a longer contact time, but still less than 2 seconds. When the cofeed to the pyrolysis reactor is a mixture of HCFC and HFC, the contact time will usually be less than 1 second, and preferably less than 0.1 second. Preferably, the conversion of the hydrochlorofluorocarbon or hydrofluorocarbon is about 10 to 50% per pass through the reaction zone, more preferably, about 20 to 40%, to minimize the formation of undesirable by-products. The feed gas to the reactor can be at a relatively low temperature, as low as ambient temperature, and such feed gas becomes heated as it traverses the length of the tubular reactor. Alternatively, the feed gas may be preheated to an elevated temperature that is less than the pyrolysis temperature of the hydrochlorofluorocarbons. This heating, together with the exothermic nature of the pyrolysis reaction occurring within the reaction zone, brings the reaction to within the desired temperature range towards the end of the reactor, with the highest temperature being encountered adjacent to the exit end of the reactor. Although the length of the reactor is heated within the pyrolysis furnace, the temperature of the pyrolysis reaction is conveniently measured by thermocouple positioned in the thermowell at the exit end of the reactor, this being the actual temperature of the reaction. The reaction temperatures disclosed herein are the gas temperatures measured at the exit end of the reactor (reaction zone). The reaction can be conveniently conducted at atmospheric pressure, but sub- and super-atmospheric pressure can also be used, such as about 0.5 to 1.5 atmospheres.

The hydrochloroflorocarbon feed to the furnace can be accompanied by other feed materials which are co-reactants, as mentioned above, or inert in the reaction within the tubular reactor. For example, an inert gas such as nitrogen or argon can be co-fed with the hydrochlorofluorocarbon to the reactor to either moderate the heat applied to the reactor or add to it. Steam may also be co-fed to the reactor.

EXAMPLES

Four reactors are used. Reactors #1, #2, and #3 are tubes, 16" (41 cm) long. Reactor #1 is made of Haynes® 242. Reactor #2 is made of Inconel® 617. Reactor #3 is made of nickel which is supported with Inconel® 617. Each tube has an ID is 0.40". The tubes are heated with two clamp-on ceramic heaters. The preheating section of each tube is 5" long and the reactor section is 2" long. Two split nickel inserts clamp on the outside of the tube in the preheater and reactor sections and the heaters are clamped on the outside of the nickel inserts. The reactor section is insulated. In the center of the preheater section (2½' (6.4 cm) from the inlet end of the tube) is a thermocouple. It is positioned in between the nickel insert and the reactor tube. The reactor section has three external thermocouples spaced 1" (2.5 cm) apart, held in position as in the preheater section. In addition, an internal platinum thermocouples (¹⁄₁₆" (6.1 mm) OD) monitor the inside bulk-gas temperatures at corresponding points on the wall of the reactor.

Feed to the reactor is controlled using calibrated mass-flow controllers. Part of the reactor exit is analyzed on line using gas chromatograph/mass spectrometer (GC/MS) and results are given in mole %.

Reactor #4 is an 18" (46 cm) length of schedule 80 Nickel 200 pipe with a weld overlay of Inconel 617. The nickel pipe OD is 1.25" (3.2 cm) and ID is 1.0" (2.5 cm). The OD of the tube with an overlay of Inconel® 617 is 1.5" (3.8 cm). The tube is positioned inside a 2½" (6.35 cm) diameter split tube furnace that was 8½" (21.6 cm) long. The heated portion of the tube furnace is 8.0" (20 cm). The midpoint of the reactor is at 4" (10 cm) and the temperature is measured by thermocouples attached to the outer wall at the mid point and also at 1" (2.5 cm) from either side of the midpoint. Corresponding internal gas temperatures are measured at these positions by an internal thermocouple.

The reactor exit gas is analyzed using GC/MS and the results are reported in mole %. The GC/MS is equipped with a 20 foot (6.1 m)×0.125 inch (3.2 mm) steel column packed with 5% Krytox® 143AC perfluoroether on ⁶⁰⁄₈₀ mesh (0.25/0.18 mm) Carbopak BHT. K programming conditions are set for a start temperature of 60° C., which is held for 3 minutes. It is then heated to 200° C. at the rate of 5° C./minute and held at 200° C. for 5 minutes. The analytical results are reported in mole %. In all the examples, product analysis shows less than 0.1% PFIB unless otherwise stated.

The bulk of the reactor effluent is scrubbed by bubbling through a pair of scrubbers in series containing 10 wt % potassium hydroxide in 50% aqueous methanol. Both scrubbers have phenolphthalein as a pH indicator and are monitored for color change, which indicates that the pH is dropping. As soon as the first scrubber in the series becomes slightly acid the scrubber solution is replaced. Unless indicated, product analysis is reported in mole %. Unidentified compounds are included in the "others" row of the tables.

In the Examples, flow rates are stated in sccm, that is, standard cubic centimeters/min, "standard" referring to standard conditions, 20° C. and atmospheric pressure. Contact times in the Examples are in the range of 60 to 100 milliseconds unless otherwise indicated.

| Reactant and Product Identification | |
|---|---|
| TFE = | tetrafluoroethylene |
| HFP = | hexafluoropropylene |
| HCFC-22 = | $CHF_2Cl$ |
| HCFC-23 = | $CHF_3$ |
| c-318 = | octafluorocyclobutane |
| HCFC-124 = | $CF_3CFHCl$ |
| HCFC-124a = | $CHF_2CF_2Cl$ |
| HFC-143a = | $CF_3CH_3$ |
| HCFC-226cb = | $CHF_2CF_2CF_2Cl$ |
| HC-1150 = | Ethylene |
| HFC-1132a = | Vinylidene fluoride ($CH_2\!=\!CF_2$) |
| PFIB = | Perfluoroisobutylene |

Pyrolysis temperature in the Examples is exit gas temperature or "Exit T int" (exit temperature internal), "Exit T Ex" being the exit wall temperature.

Example 1

Table 1 summarizes the reaction conditions and results of pyrolysis of HCFC-22 in Reactor #1 (Haynes® 242), #2 (Inconel® 617), and #3 (nickel with a weld overlay of Inconel® 617). Useful products are TFE, HFP, which are important monomers, and c-318, HCFC-124a, and HCFC-226cb, which can be further pyrolyzed to yield TFE and/or HFP. The internal exit temperature, e.g. 722° C. for Reactor #4, is considered the pyrolysis reactor temperature.

TABLE 1

HFC-22 (CF$_2$HCl) Pyrolysis in Nickel Alloy and Nickel-lined Reactors

| Material of Construction | Reactor #1 Haynes ® 242 | Reactor #2 Inconel ® 617 | Reactor #3 Nickel-lined Inconel 617 | Reactor #3 Nickel-lined Inconel 617 |
|---|---|---|---|---|
| Preheater T | 550/— | 550/— | 550/— | 550/— |
| Inlet T Ex/Int | 774/690 | 753/689 | 738/665 | 718/652 |
| Mid T Ex/Int | 784/736 | 763/731 | 763/710 | 738/691 |
| Exit T Ex/Int | 784/722 | 766/725 | 752/714 | 727/692 |
| HCFC-22 sccm | 500 | 500 | 500 | 500 |
| GC Exit Results Mole % | | | | |
| TFE | 26.9 | 29.0 | 31.4 | 24.0 |
| HCFC-22 | 68.4 | 65.7 | 64.7 | 73.7 |
| HFP | 0.6 | 0.8 | 0.6 | 0.3 |
| c-318 | 1.4 | 1.6 | 1.3 | 0.7 |
| 226cb | 0.5 | 0.5 | 0.4 | 0.3 |
| Other | 2.2 | 2.4 | 1.5 | 0.9 |
| Useful Products TFE + HFP + 124a + c-318 + 226cb | 30.6 | 33.1 | 34.6 | 25.8 |
| Conversion | 31.6 | 34.3 | 35.3 | 26.3 |
| Selectivity % | 96.8 | 96.5 | 98.0 | 98.1 |

The nickel-lined reactor (#3) provides significantly greater selectivity to useful products than the nickel alloy reactors #1 and #2. At an internal exit temperature of 714° C. the nickel-lined tube gives higher conversion of HCFC-22 than do the Haynes or Inconel alloys, even though they are run at higher temperatures, 722° C. and 725° C.

Example 2

HCFC-22 is pyrolyzed in Reactor #4, a nickel-lined, Inconel 617 supported tube. Table 2 summarizes the results. At exit gas temperatures of 606° C., 652° C., and 705° C. high selectivity to useful product is obtained. At 763° C., above the temperatures according to this patent, selectivity declines and PFIB is first seen.

TABLE 2

Pyrolysis of HCFC-22

| Inlet, wall temp | 623° C. | 674° C. | 727° C. | 771° C. |
|---|---|---|---|---|
| Middle, wall temp | 640° C. | 693° C. | 747° C. | 794° C. |
| Exit wall temp | 647° C. | 701° C. | 757° C. | 805° C. |
| Inlet gas temp | 593° C. | 640° C. | 687° C. | 731° C. |
| Middle gas temp | 604° C. | 651° C. | 700° C. | 751° C. |
| Exit gas temp | 606° C. | 652° C. | 705° C. | 763° C. |
| HCFC-22 Feed sccm | 1000 | 1000 | 1000 | 1000 |
| GC Results in Mole % | | | | |
| HFC-23 | 0.1 | 0.1 | 0.3 | 1.7 |
| TFE | 6.3 | 15.6 | 25.2 | 16.1 |
| HCFC-22 | 92.6 | 79.0 | 48.0 | 22.7 |
| HFP | 0.1 | 0.4 | 2.6 | 13.4 |
| HCFC-124a | 0.2 | 1.4 | 10.3 | 20.9 |
| HCFC-124 | 0.0 | 0.1 | 0.6 | 3.3 |
| c-318 | 0.2 | 1.4 | 6.4 | 6.8 |
| PFIB | 0.0 | 0.0 | 0.0 | 0.8 |
| HCFC-226cb | 0.2 | 0.8 | 2.5 | 2.0 |

TABLE 2-continued

Pyrolysis of HCFC-22

| Others | 0.30 | 1.2 | 3.7 | 11.8 |
|---|---|---|---|---|
| HCFC-22 Conversion | 7.4% | 21.0% | 52.0% | 77.3% |

Example 3

Using Reactor #4, equal amounts of HCFC-22 and HCFC-124 are fed, with temperature controlled so that the exit gas temperature is 608° C.

TABLE 3

Pyrolysis of HCFC-22 and HCFC-124

| Inlet, wall temp | 624° C. |
|---|---|
| Middle, wall temp | 650° C. |
| Exit wall temp | 644° C. |
| Inlet gas temp | 587° C. |
| Middle gas temp | 605° C. |
| Exit gas temp | 608° C. |
| HCFC-22 Feed sccm | 500 |
| HCFC-124a Feed sccm | 500 |
| GC Results in Mole % | |
| TFE | 4.0 |
| HCFC-22 | 42.9 |
| HFP | 0.2 |
| HCFC-124a | 0.1 |
| HCFC-124 | 52.7 |
| c-318 | 0.0 |
| PFIB | 0.0 |
| HCFC-226cb | 0.0 |
| Others | 0.0 |
| HCFC-22 Conversion | 7.1% |

At pyrolysis temperatures of 650° C., greater amounts of TFE and HFP with high selectivity to useful products are obtained.

Example 4

HCFC-124a is fed to Reactor #4 at 646° C., at 694° C., and at 747° C. Conversion increases with temperature, good selectivity, 76%, being shown even at 747° C. Pyrolysis at 799° C. results in formation of 2.7% PFIB, nine times the amount formed in the 747° C. pyrolysis.

TABLE 4

Pyrolysis of HCFC-124a (CHF$_2$CF$_2$Cl)

| Inlet wall temp | 643° C. | 698° C. | 752° C. |
|---|---|---|---|
| Middle wall temp | 665° C. | 719° C. | 774° C. |
| Exit wall temp | 669° C. | 724° C. | 780° C. |
| Inlet gas temp | 642° C. | 695° C. | 742° C. |
| Middle gas temp | 651° C. | 701° C. | 751° C. |
| Exit gas temp | 646° C. | 694° C. | 747° C. |
| 124a Feed sccm | 200 | 200 | 200 |
| He Feed sccm | 800 | 800 | 800 |
| GC Results in Mole % | | | |
| HCFC-23 | 0.0 | 0.1 | 0.6 |
| TFE | 2.2 | 18.1 | 38.3 |

TABLE 4-continued

Pyrolysis of HCFC-124a (CHF$_2$CF$_2$Cl)

| | | | |
|---|---|---|---|
| HCFC-22 | 0.1 | 1.7 | 7.2 |
| HCFC-143 | 0.0 | 0.0 | 0.0 |
| HFP | 0.1 | 0.9 | 7.1 |
| HCFC-124a | 94.7 | 75.1 | 33.4 |
| 124 | 2.4 | 1.9 | 1.7 |
| C318 | 0.0 | 0.8 | 5.2 |
| PFIB | 0.0 | 0.0 | 0.3 |
| HCFC-226cb | 0.0 | 0.0 | 0.3 |
| Others | 0.30 | 1.10 | 5.70 |
| HCFC-124a Conversion | 5.3% | 24.9% | 66.6% |

Example 5

Reactor #4 is used for pyrolysis of HFC-143a at about 790–800° C. (The exit gas temperatures for the pyrolyses in columns 3 and 4 are not available, but it can be inferred from column 2 that exit gas temperature is about 100 lower than the middle gas temperature.) This hydrofluorocarbon is a precursor to vinylidene fluoride in pyrolytic reactions. Pyrolyses are conducted with 4:1, 2:1, and 1:1 helium dilution. The effect of added helium is to reduce HFC-143a residence time (contact time) in the reactor, thereby reducing conversion. As the results summarized in Table 5, show, in the nickel-lined tube according to this invention, HFC-143a pyrolyzes to vinylidene fluoride in high yield with few side products even at 40+% conversion.

TABLE 5

Pyrolysis of HFC-143a (CF$_3$CH$_3$)

| | | | |
|---|---|---|---|
| Inlet wall temp | 812° C. | NA | NA |
| Middle wall temp | 837° C. | NA | NA |
| Exit wall temp | 828° C. | NA | NA |
| Inlet gas temp | 803° C. | NA | NA |
| Middle gas temp | 809° C. | 804 | 805 |
| Exit gas temp | 799° C. | NA | NA |
| 143a Feed sccm | 200 | 200 | 200 |
| He Feed sccm | 800 | 400 | 200 |
| GC Results in Mole % | | | |
| HFC-23 | 0.1 | 0.2 | 0.4 |
| 1150 (CH$_2$=CH$_2$) | 0.0 | 0.0 | 0.0 |
| 1132a (CH$_2$=CF$_2$) | 22.2 | 29.6 | 40.1 |
| 143a | 77.4 | 69.6 | 58.0 |
| Other | 0.2 | 0.5 | 1.4 |
| Conversion | 22.6% | 30.4% | 42% |
| Vinylidene fluoride | 22.2% | 29.6% | 40.1% |

Example 6

In Reactor #4 HFC-23 and c-318 are copyrolyzed at about 885° C. to yield TFE and HFP with about 5% PFIB formation based on HFP produced. When the production of HFP is at least ten times that of PFIB, the pyrolysis result (selectivity) is excellent.

TABLE 6

Pyrolysis of HFC-23 + c-381

| | | |
|---|---|---|
| Inlet wall temp | 717° C. | 696° C. |
| Middle wall temp | 796° C. | 782° C. |
| Exit wall temp | 834° C. | 825° C. |
| Inlet gas temp | 858° C. | 854° C. |
| Middle gas temp | 881° C. | 881° C. |
| Exit gas temp | 887° C. | 884° C. |
| HFC-23 Feed sccm | 500 | 440 |
| c-318 Feed sccm | 375 | 440 |
| He Feed sccm | 1000 | 1000 |
| Residence time (s) | 1.32 | 1.33 |
| GC result mole % | | |
| HFC-23 | 41.1 | 35.2 |
| TFE | 22.4 | 25.2 |
| HFP | 24.9 | 25.6 |
| c-318 | 2.1 | 3.3 |
| PEIB | 1.4 | 1.5 |
| Other | 6.9 | 7.8 |
| PFIB/HFP % | 5.5 | 5.7 |
| HFC-23 conversion % | 34.3% | 29.6% |

What is claimed is:

1. Process comprising pyrolyzing hydrochlorofluorocarbon or hydrofluorocarbon to fluoromonomer, said pyrolyzing being carried out in a reaction zone lined with mechanically supported nickel.

2. The process of claim 1 wherein said hydrochlorofluorocarbon includes chlorodifluoromethane.

3. The process of claim 2 wherein said hydrochlorofluorocarbon also includes CF$_2$ClCF$_2$H.

4. The process of claim 1 wherein said pyrolysis is carried out to a conversion of said hydrochlorofluorocarbon of about 10 to 50%.

5. The process of claim 1 wherein said pyrolysis is carried out at a temperature of about 600° C. to 750° C., with the proviso that when said hydrofluorocarbon is being pyrolyzed the temperature is about 750° C. to 900° C.

6. The process of claim 1 wherein said pyrolysis is carried out at a residence time in said reaction zone of less than about 0.1 second, with the proviso that when said hydrofluorocarbon is being pyrolyzed the residence time is less than about 2 seconds.

7. The process of claim 1 wherein said fluoromonomer includes tetrafluoroethylene.

8. The process of claim 1 wherein said reaction zone is tubular in cross-section and the mechanical support for said nickel lining is a metal jacket for said lining.

9. The process of claim 1 wherein said reaction zone is annular in cross-section.

10. The process of claim 1 wherein said reaction zone has a volume of at least about 0.04 m$^3$.

11. The process of claim 1 wherein said reaction zone has a length of at least about 8 m.

* * * * *